US009474635B2

(12) United States Patent
Egilsson et al.

(10) Patent No.: US 9,474,635 B2
(45) Date of Patent: Oct. 25, 2016

(54) BRIM ATTACHMENT WITH A SEAL ELEMENT FOR A PROSTHETIC SOCKET

(71) Applicant: OSSUR HF, Reykjavik (IS)

(72) Inventors: Egill Sveinbjorn Egilsson, Reykjavik (IS); Grimur Jonsson, Vogar (IS)

(73) Assignee: OSSUR HF, Reykjavik (IS)

( * ) Notice: Subject to any disclaimer, the term of this patent is extended or adjusted under 35 U.S.C. 154(b) by 67 days.

(21) Appl. No.: 14/457,379

(22) Filed: Aug. 12, 2014

(65) Prior Publication Data

US 2015/0051711 A1 Feb. 19, 2015

Related U.S. Application Data

(60) Provisional application No. 61/865,175, filed on Aug. 13, 2013.

(51) Int. Cl.
*A61F 2/78* (2006.01)
*A61F 2/80* (2006.01)
*A61F 2/76* (2006.01)

(52) U.S. Cl.
CPC . *A61F 2/80* (2013.01); *A61F 2/78* (2013.01); *A61F 2/76* (2013.01); *A61F 2002/7837* (2013.01); *A61F 2002/802* (2013.01)

(58) Field of Classification Search
CPC .................. A61F 2002/748; A61F 2002/7837; A61F 2002/802; A61F 2002/805
USPC ...................................................... 623/32, 34
See application file for complete search history.

(56) References Cited

U.S. PATENT DOCUMENTS

| 1,497,219 | A |   | 6/1924  | Martino           |        |
|-----------|---|---|---------|-------------------|--------|
| 3,309,714 | A |   | 3/1967  | Porten            |        |
| 4,479,272 | A |   | 10/1984 | Beldzisky         |        |
| 4,908,037 | A | * | 3/1990  | Ross              | 623/32 |
| 4,955,920 | A |   | 9/1990  | Wellershaus et al.|        |
| 5,314,497 | A |   | 5/1994  | Fay et al.        |        |
| 7,169,188 | B2|   | 1/2007  | Carstens          |        |
| 7,662,191 | B2|   | 2/2010  | Asgeirsson        |        |

(Continued)

FOREIGN PATENT DOCUMENTS

| FR | 525 870 A      | 9/1921  |
| WO | 2008/040291 A1 | 4/2008  |
| WO | 2012/142627 A2 | 10/2012 |
| WO | 2013/064240 A1 | 5/2013  |

OTHER PUBLICATIONS

International Search Report and the Written Opinion of the International Searching Authority from corresponding International Application No. PCT/US2014/050656, Oct. 29, 2014.

*Primary Examiner* — David H Willse
(74) *Attorney, Agent, or Firm* — Workman Nydegger (57) ABSTRACT

A brim attachment for a prosthetic socket includes a cuff section defining an upper portion of the brim attachment and is arranged to extend about and upwardly from a socket opening. The cuff section is configured to move between tensioned and relaxed positions, wherein the tensioned position the cuff section is arranged to fold away from the socket opening, wherein the relaxed position the cuff section is arranged to extend above the socket opening and generally concentric with an outer surface of the socket. An interface section defines a lower portion of the brim attachment and is arranged to extend along a surface of the socket. The brim attachment may include a seal element protruding toward a central axis of the socket.

13 Claims, 5 Drawing Sheets

(56) References Cited

U.S. PATENT DOCUMENTS

2004/0243252 A1  12/2004  Carstens
2008/0086218 A1  4/2008   Egilsson
2011/0112656 A1  5/2011   Kurth
2011/0160872 A1  6/2011   Westrate

* cited by examiner

BRIM ATTACHMENT WITH A SEAL ELEMENT FOR A PROSTHETIC SOCKET

FIELD OF ART

The disclosure relates to the field of prosthetic devices, and more particularly to a brim attachment with a seal element for a prosthetic socket.

BACKGROUND

With advancements in prosthetic components, improved suspension solutions have become a pressing need. Improved methods and apparatuses for creating a seal between a prosthetic limb and a residual limb can provide significant improvements in motion and comfort for wearers of prosthetic limbs.

A seal in the sense of a suspension solution may refer to a component of a prosthetic limb that allows a vacuum to be formed between a residual limb and a socket for receiving a prosthetic limb. In prosthetic systems, a vacuum may not be applied directly to the skin, but rather between the socket and a skin interface, such as a suspension liner. A seal element may be positioned to create a vacuum between the socket and the liner. A seal element may be placed so the vacuum is created at least between a distal portion of the residual limb and the corresponding portion of the socket.

An example of a socket, as is readily understood by the skilled artisan in the field of prosthetics, is described in U.S. Pat. No. 7,438,843, granted Oct. 21, 2008, the entirety of which is incorporated herein by reference. The liner may be formed under any of the following U.S. Pat. No. 6,136,039, granted Oct. 24, 2000, U.S. Pat. No. 6,626,952, granted Sep. 30, 2003, and U.S. Pat. No. 7,118,602, granted Oct. 10, 2006, each of which is incorporated by reference in its entirety. A prosthetic sleeve 200 can create a seal between the socket 108 and the liner 112, as disclosed in U.S. Pat. No. 8,097,043, granted Jan. 17, 2012 and incorporated by reference in its entirety.

A significant drawback to known vacuum solutions is they fail to adapt to limb volume change, which occurs when a user is walking. Yet another drawback is that it may be difficult or cumbersome to remove a prosthetic device after a vacuum has been formed.

There is a need for a prosthetic device, system and method that provides a vacuum solution adaptable to a residual limb during normal use. There is also a need to provide a vacuum solution allowing a prosthetic limb to be easily removed after a vacuum has been formed.

SUMMARY

According to various embodiments, a brim attachment is arranged for securing to a prosthetic socket, and is configured for tensioned and relaxed positions. The brim attachment is configured to secure about an upper or proximal perimeter of the socket, and extend over, beyond or secure to inner and outer surfaces of the socket.

In an embodiment, the brim attachment defines a cuff section defining an upper portion of the brim attachment and is arranged to extend about and upwardly from the socket opening. The cuff section is configured to move between tensioned and relaxed positions. In the tensioned position the cuff section is arranged to fold away from the socket opening, whereas in the relaxed position the cuff section is arranged to extend above the socket opening and generally concentric with the outer surface of the socket. The cuff section may be flexible relative to the socket, which may be hard and rigid or semi-rigid such that the cuff section substantially flexes relative to the socket.

The brim attachment also includes an interface section defining a lower portion of the brim attachment and is arranged to extend along the inner surface of the socket. The interface section may be arranged to extend flush against the inner surface of the socket, and the socket may include a recess extending into the thickness of the socket and relative to areas outside the recess. The interface section fits within the recess and the inner surface of the socket in combination with areas of the inner surface of the socket outside the recess define a continuous inner surface within interruption.

In the tensioned position, the cuff section may be arranged to fold downwardly away from the opening and generally over the outer surface of the socket. The cuff and interface sections may be formed integrally with one another from the same material. The brim attachment may be formed as a molded, such as by injection molding, elastomeric material.

The cuff section may define an asymmetrical upper edge having a maximum height extending a greater distance from the socket opening than a minimum height of the upper edge. The maximum height may be at a first side of the socket and the minimum height is at a side opposite the maximum height. The upper edge tapers in height from the maximum height to the minimum height. The interface section may have a thickness smaller than a thickness of the cuff section, particularly since according to a variation the interface section may form part of the thickness of the socket so the combined thickness of the interface section and the recessed section of the socket is the same as the thickness of the socket outside of the recessed section.

The brim attachment may include a seal element or a plurality of seal elements for engagement with a residual limb or a liner. According to an embodiment, the seal element may be arranged to protrude toward a central axis of the socket from an inner surface of the brim attachment when the brim attachment is in the relaxed position. The seal element may be above the interface section and extend above the socket opening.

According to a variation of the seal element, the seal element defines a tapered thickness with a peak defined at an outermost portion of the seal element and forming the thinnest portion of the seal element. The seal element may have a base portion formed integrally with the cuff and interface sections, whereas the base portion may form the thickest portion of the seal element.

In a variation in the tensioned position, the seal element preferably protrudes upwardly from the socket opening and generally concentrically with the outer surface of the socket. In the relaxed position, the seal element is arranged to flexibly bias into the socket opening and extend obliquely toward the central axis.

The cuff section may be arranged to extend circumferentially about and upwardly away from an upper perimeter of the socket opening in the relaxed configuration. The interface section may extend downwardly from the cuff section. The cuff section may be arranged to extend circumferentially about and upwardly away from an upper perimeter of the socket opening in the relaxed configuration. The interface section extends downwardly from the cuff section and concentrically with the cuff section. The seal element extends generally concentric with the interface section in the tensioned position.

In a variation, the seal element may be arranged to obliquely extend toward a central axis of the socket in the relaxed position, and arranged to extend generally concentric to the outer surface of the socket in the tensioned position. The seal element may be arranged to move into the relaxed and tensioned positions as a result of moving the cuff section between the relaxed and tensioned positions.

Various methods include placing a residual limb in the socket so as to place the cuff and seal element in the tensioned and relaxed positions to secure a residual limb to a prosthetic socket with the brim attachment. Other methods may include installing the brim attachment to a prosthetic socket such as by securing the interface section to an interior surface of the prosthetic socket. The interface section may be adhered to the interior surface, or in alternative methods the interface section may be secured over an exterior surface of the prosthetic socket. The prosthetic socket may be adapted by removing a thickness of the prosthetic socket to create a recess for receiving the interface section, such as at or near the opening of the socket.

BRIEF DESCRIPTION OF THE DRAWINGS

The prosthetic device is described referring to the accompanying drawings which show preferred embodiments according to the device described. The device, system and method as disclosed in the accompanying drawings are illustrated for example only. The elements and combinations of elements described below and illustrated in the drawings can be arranged and organized differently to result in embodiments still within the spirit and scope of the device described.

DETAILED DESCRIPTION OF VARIOUS EMBODIMENTS

A better understanding of different embodiments of the prosthetic device may be gained from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the specific embodiments disclosed, but on the contrary, the invention covers all modifications, alternative constructions, combinations, and equivalents falling within the spirit and scope of the disclosure and defined by the appended claims.

It will be understood that, unless a term is defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a function, is not to be interpreted as a "means" or "step" clause as specified in 35 U.S.C. §112, paragraph 6.

Figure 1A:
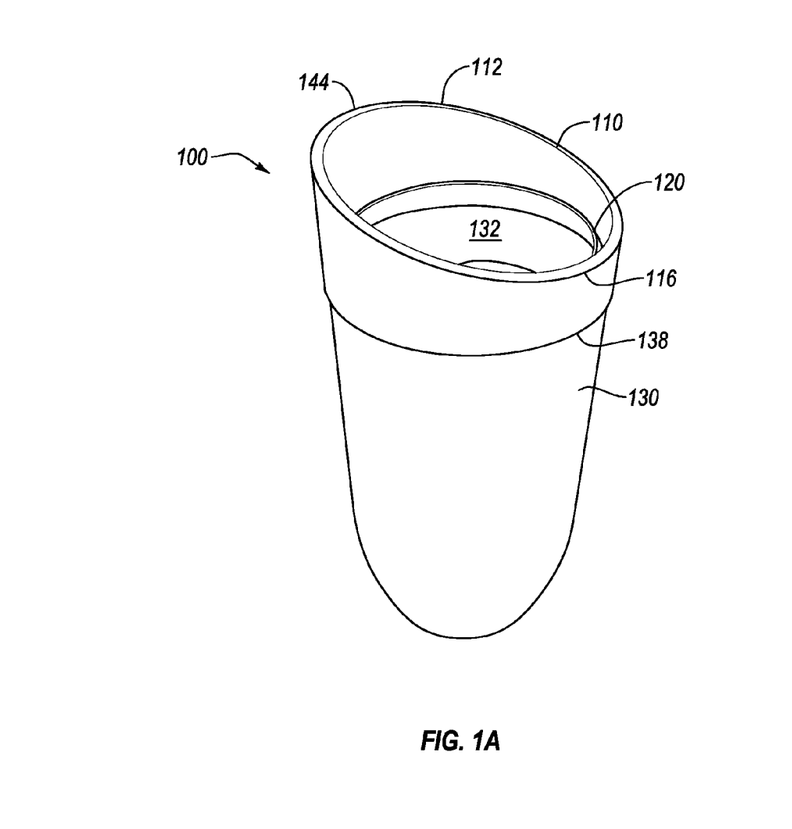
FIG. 1A shows a front view of an embodiment of a socket and attached brim attachment.

FIG. 1A illustrates an embodiment of the socket 130 and a brim attachment 100. In this embodiment. The socket 130 defines an opening 132, outer and inner surfaces 135, 136, with a central axis A-A.

The brim attachment 100 includes a cuff section 110 and a seal element 120. In a variation, the cuff section 110 and the seal element 120 can be incorporated into a single elastomeric structure. The cuff section 110 and seal element 120 are sufficiently elastic and resilient to allow the cuff section 110 and seal element 120 to return to relaxed positions after they are bent and/or stretched. The brim attachment 100 and the cuff section 110 can be ergonomically formed so the brim attachment 100 comfortably fits over a residual limb whether or not donning a liner when inserted into the socket 130.

The height of the brim attachment 100 may be biased to one side such that the brim attachment 100 is shorter over a section that will fit against a wearer's inner leg and taller over a section that will fit against a wearer's outer leg. The cuff section 110 may define an asymmetrical upper edge 112 having a maximum height 114 extending a greater distance from the socket opening 132 than a minimum height 116 of the upper edge 112. The maximum height 114 may be at a first side of the socket 130 and the minimum height 116 is at a side opposite the maximum height 114. The upper edge 112 may taper in height from the maximum height 114 to the minimum height 116. One will understand that various other physical adjustments can be made to the size and shape of the brim attachment 100 to further increase the ergonomics of the device.

Figure 1B:
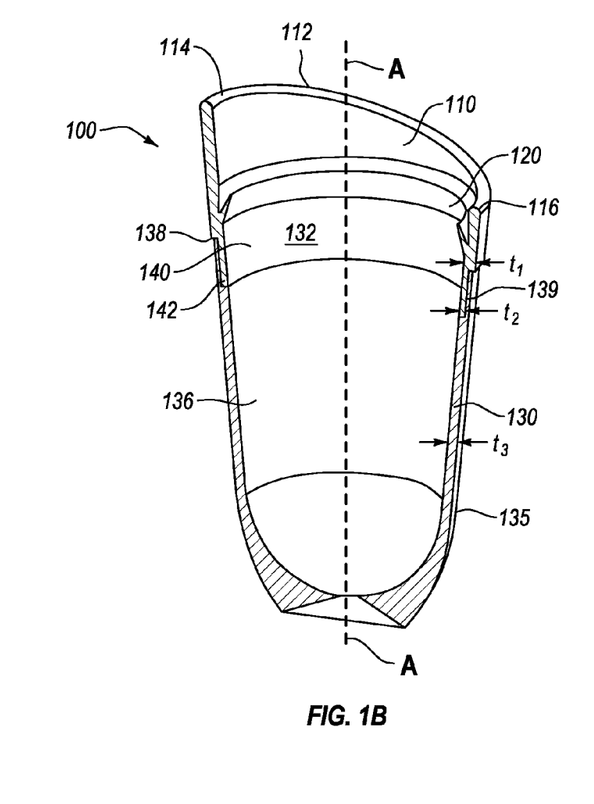
FIG. 1B shows a cross sectional view of the socket and attached brim attachment from FIG. 1A.

FIG. 1B illustrates a cross sectional view of the socket 130 and attached brim attachment 100 from FIG. 1A. As depicted in FIG. 1B, the brim attachment 100 can also include an interface section 140. In at least one embodiment, the interface section 140 can allow the same brim attachment 100 to be used with a variety of sizes and shapes of sockets 130.

The interface section 140 depicted in FIG. 1B may comprise an elastomeric lip 142 that is insertable into a recess 139 formed by the socket 130 proximate the opening 132. The lip 142 may be adhered along the inner surface 136 of the socket 130, and is flush with the inner surface 136 of the socket 130 in areas outside of the recess 139 so the socket 130 defines a continuous inner surface 136 with the interface section 140. A thickness t3 of the socket outside of the recess 139 may be the same as the combined thickness of the socket wall at the recess 139 and the lip 142.

While exemplified as located along or from the inner surface 136 of the socket, the recess 139 may be located from the outer surface 135 so the interface section 140 is tensioned over the socket 130. The lip 142 is reversed to be tensioned over the outer surface 135 of the socket, whether or not there is a corresponding recess. The interface section 140 that may be connectable to generic sockets 130 is not manufactured to interface with a brim attachment 100.

In the embodiment of FIG. 1B, the interface section 140 has a smaller thickness t2 than a thickness t1 of the cuff section 110. The interface section 140 may be provided with or without the lip 142, and rather define a continuous thickness, either the same or different from the thickness of the cuff section 110.

As depicted in FIG. 1A and FIG. 1B, the cuff 110 and seal element 120 are in a relaxed position. The cuff section 110 and seal element 120 are generally not under tension, and are positioned in their respective natural states. As shown in FIG. 1B, when in a relaxed position, the cuff section 110 extends upwards from the socket 130, and the seal element 120 extends inwardly towards the middle of the opening of the socket 130. In at least one embodiment, when in a relaxed position, the seal element 120 can function as a seal around a liner (not shown) inserted into the socket 130.

Figure 2A:
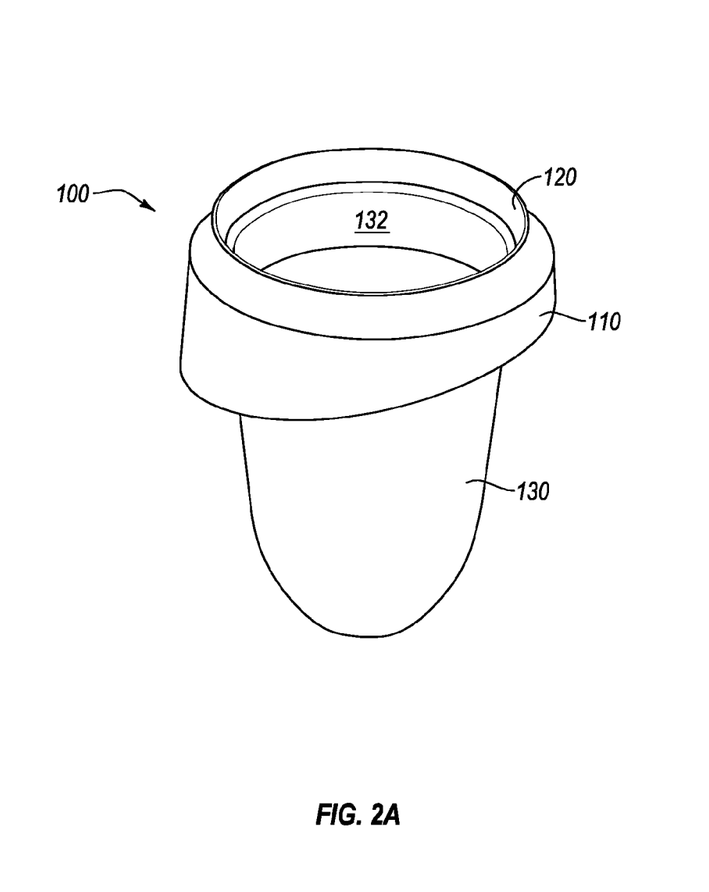
FIG. 2A shows another front view of an embodiment of a socket and attached brim attachment.
Figure 2B:
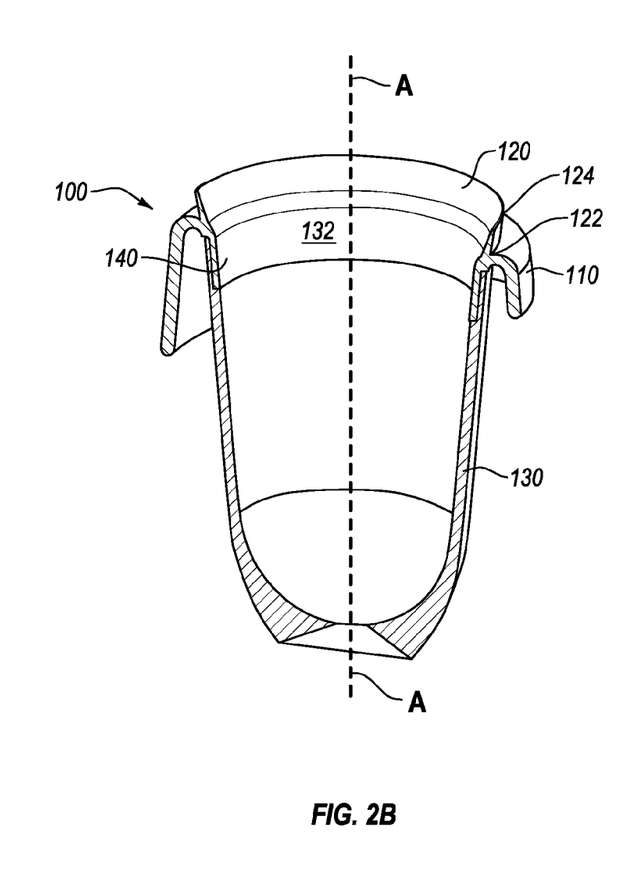
FIG. 2B shows another cross sectional view of the socket and attached brim attachment from FIG. 2A.

FIG. 2A and FIG. 2B illustrate views of the socket 130 and attached brim attachment 100 from FIGS. 1A and 1B where the brim attachment 100 is in a tensioned position. In this embodiment, the cuff section 110 has been reflected, or folded outward from the proximal opening of the socket 130, such that the cuff section 110 and seal element 120 are in a tensioned position. In at least one embodiment, once the cuff section 110 is rolled over itself it will remain in the tensioned position with no additional effort from a user until the user rolls the cuff section 110 back to the relaxed position.

In FIGS. 2A and 2B, the seal element 120 is also in a tensioned position. As depicted, when in the tensioned position, the seal element 120 generally does not extend inwardly towards the middle of the opening of the socket 130, as shown in FIG. 1B. In this embodiment, the seal element 120 now extends outward and upward from the opening of the socket 130. One will understand that in this configuration the seal element 120 would not likely form a seal with a liner and residual limb (not shown) placed within the socket 130. In the depicted configuration, a wearer of the prosthetic limb can also easily slide a liner and residual limb into the socket 130 or remove a liner and residual limb from the socket 130.

According to FIGS. 1A-2B, the seal element 120 is arranged to protrude toward a central axis A-A of the socket 130 from an inner surface of the brim attachment 100 when the brim attachment 100 is in the relaxed position. The seal element 120 is preferably above the interface section 140 and extends above the socket opening 132. In other variations, however, the seal element 120 may be positioned lower relative to the socket opening 132, such that the seal element 120 protrudes along the height of the inner surface of the socket 130 such as from the interface section 140. Alternatively, the seal element 120 may form a plurality of seals lined along or across both the interface and cuff sections.

The seal element 120 may include a single seal or seals, and may define a variety of different shapes. Various shapes of the seal elements are found in at least U.S. Pat. No. 7,025,793, granted on Apr. 11, 2006, U.S. Pat. No. 8,034,120, granted on Oct. 11, 2011, and U.S. Pat. No. 8,372,159, granted Feb. 12, 2013, each incorporated by reference.

According to the depicted embodiment, the seal element 120 includes a tapered thickness with a peak 124 defined at an outermost portion of the seal element 120 and forming the thinnest portion of the seal element 120. The seal element 120 defines a base portion 122 formed integrally with the cuff and interface sections 110, 140, with the base portion 122 forming the thickest portion of the seal element 120.

In the tensioned position, the seal element 120 protrudes upwardly from the socket opening 132 and is concentric with the outer surface 135 of the socket 130. In the relaxed position, the seal element 120 is arranged to flexibly bias into the socket opening 132 and extend obliquely toward the central axis A-A. The seal element 120 is arranged to extend generally concentric to the outer surface of the socket 130 in the tensioned position, and is arranged to move into the relaxed and tensioned positions because of moving the cuff section 110 between the relaxed and tensioned positions. The cuff section 110 is arranged to extend circumferentially about and upwardly away from an upper perimeter 138 of the socket opening 132 in the relaxed configuration with the interface section 140 extending downwardly from the cuff section 110.

The seal element 120 is adapted to function in a reverse manner to the seal elements in the above-cited prior art documents located along a liner and adapted to engage an inner surface of socket, rather than extending from an inner surface of a socket to engage a liner or residual limb.

In use, a residual limb is placed within a liner, and both the residual limb and the liner sleeve body portion are inserted within a hard socket of a prosthetic system so the seal element engages an outer surface of the liner to isolate the distal end area of the hard socket from surrounding atmosphere. Creation of a hypobaric pressure within the distal end area of the hard socket or simple evacuation or venting of air between the distal end area of the liner and the distal end of the hard socket serves to effectively retain the liner within the socket, with the seal element isolating the distal end of the socket externally of the liner from atmosphere.

Whether a hypobaric pressure is created within the distal end area of the socket or if the distal end is merely isolated from atmosphere, withdrawal of the liner and the residual limb contained will be resisted strongly by the creation of or maintenance of a suction between the distal end of liner and the interior distal end area of the socket when a pulling force extricating the liner from the socket is applied. The suction may be released between the socket and the liner by exposing the interior distal end area of the socket to atmosphere.

The seal element provides a positive sealing effect by its resilient compression between the brim attachment and the liner due to the radial force of the residual limb within the liner. The peripherally extending seal element takes up irregularities between the exterior of the liner and the interior of the socket irrespective of bony protuberances, irregularities and non-cylindrical forms of the residual limb. Because the socket is already configured to closely approximate the exterior shape of the residual limb, the seal element simply follows the contour of the inner surface of the socket to isolate the distal end of the socket from atmosphere when the liner is inserted into the socket.

When the seal element encounters the liner, the seal element is compressed to bridge a seal between the liner and the socket 130. In a compressed state, the angle at which the seal element extends relative to the central axis A-A reduces relative to when the liner is not inserted into the socket and when the seal element is in the relaxed position.

Figure 3:
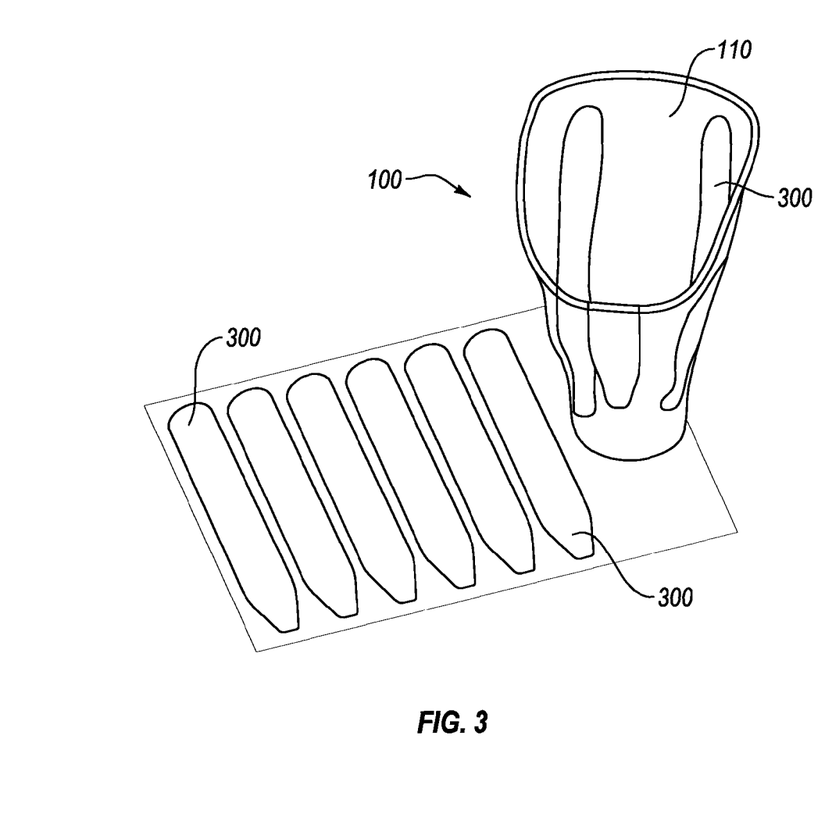
FIG. 3 shows an embodiment of a brim attachment comprising uni-directional material.

FIG. 3 shows an alternate embodiment of a brim attachment 100 comprising a uni-directional material 300 functioning as a liner interface. A uni-directional material 300 comprises biased direction texture that provides grip in one direction while providing free glide in the opposite direction. As used in at least one embodiment of the disclosure, the uni-directional material 300 can comprise texture that allows a liner and accompanying residual limb to slide past the uni-directional material disposed on a brim attachment 100 and into a socket 130, while then resisting the liner and accompanying residual limb from being pulled out of the socket 130.

The uni-directional material 300 can be disposed around the entire inner-circumference of the brim attachment 100 or it can be formed in strips that run longitudinally down the length of the brim attachment 100. In at least one implementation, the brim attachment 100 and the socket 130 can be integrated, and the uni-directional material 300 can be disposed within at least a portion of the interior of the socket 130. Using the uni-direction material 300 within the soft cuff 110 can provide a wearer with additional proprioception and ease of donning.

In at least one embodiment, a brim attachment 100 can comprise both uni-directional material 300 and a sealing seal element 120. Alternate embodiments can comprise just the uni-directional material 300 or just the sealing seal element 120. Regardless of whether the liner interface comprises a seal element 120, uni-directional material 300, or both, the folding, or reflecting, of the flexible brim 110 can disengage the liner interface (i.e., seal element 110 of uni-directional material 300) from a liner and residual limb inserted into the socket 130.

Similar to the embodiment depicted in FIG. 2B, if the flexible cuff 110 is folded away from the opening of the socket 130 the uni-directional material 300 lining the interior of the brim attachment 100 would also be pulled away from the opening of the socket 130, and accordingly away from a liner and residual limb that also may be disposed within the socket 130. In this way, a brim attachment 100 comprising uni-directional material 300 can easily be doffed by reflecting the cuff section 110, and then sliding the residual limb and liner out of the socket 130.

Figure 4:
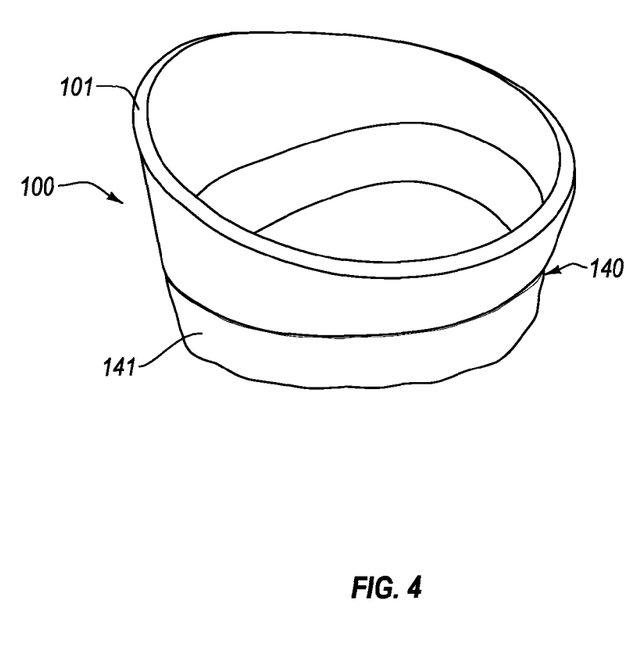
FIG. 4 shows an embodiment of a brim attachment.

FIG. 4 illustrates an embodiment of a brim attachment 100 detached from a socket 130. An interface section 140 is depicted. In at least one embodiment, the interface section 140 can connect to and interface with a variety of sockets 130. As shown, the interface section 140 can comprise a circular rim that engages with an interior circumferential surface of a socket 130. The circular rim can comprise a rigid portion that extends circumferentially around the interface section 140. The rigid portion can be sized to be slightly larger than an interior circumference of a socket 130, such that the rigid portion forms a press-fit connection between the brim attachment 100 and a socket 130.

The interface section 140 can also comprise an elastic rim that fits over an external circumferential surface of a socket 130. The interface section 140 can be stretched over the outside of a socket 130 to create a seal between the brim attachment 100 and the socket 130. Further, in at least one embodiment, the interface section 140 can be glued or otherwise adhered to a surface of the socket 130. Further still, the brim attachment 100 can be formed into the socket 130. In an embodiment where a vacuum is formed within the socket 130, one will understand that the interface section 140 must form an airtight connection with the socket 130. The interface section 140 must also be durable enough to withstand pressures and forces associated with normal use of a prosthetic limb walking.

The interface section 140 may comprise a textile 141 that connects the silicone based brim attachment 101 to material used to form the socket 130. Sometimes, silicone cannot by itself bond to materials used to form the socket, such as polyurethane. However, the textile 141 bonds to silicone, either as being partially embedded (at least in part due to its porosity) to the end of the silicone brim 101, or glued to the silicone. The textile 141 can be embedded within the materials used to form the socket or interleaved with fiber reinforcing layers forming part of a socket. The interface section 140 therefore can be prefabricated and added during socket fabrication.

Figure 5:
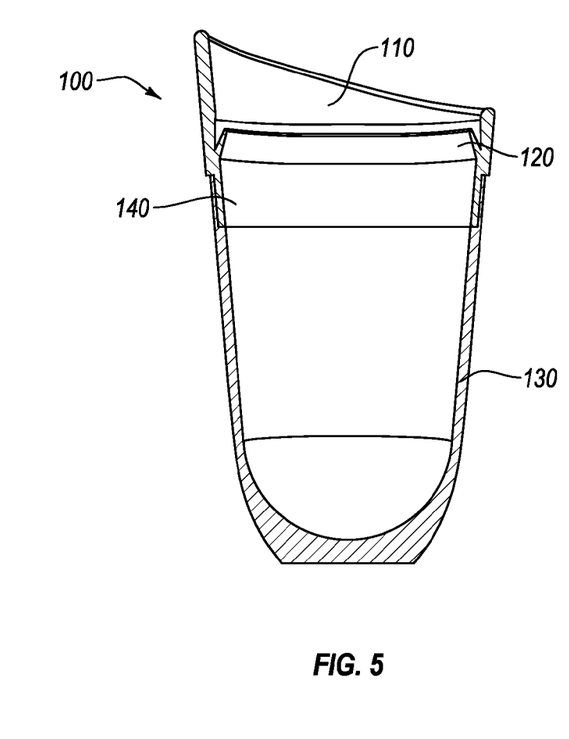
FIG. 5 shows a cross sectional view of an embodiment of a socket and attached brim attachment with the brim in a relaxed position.
Figure 6:
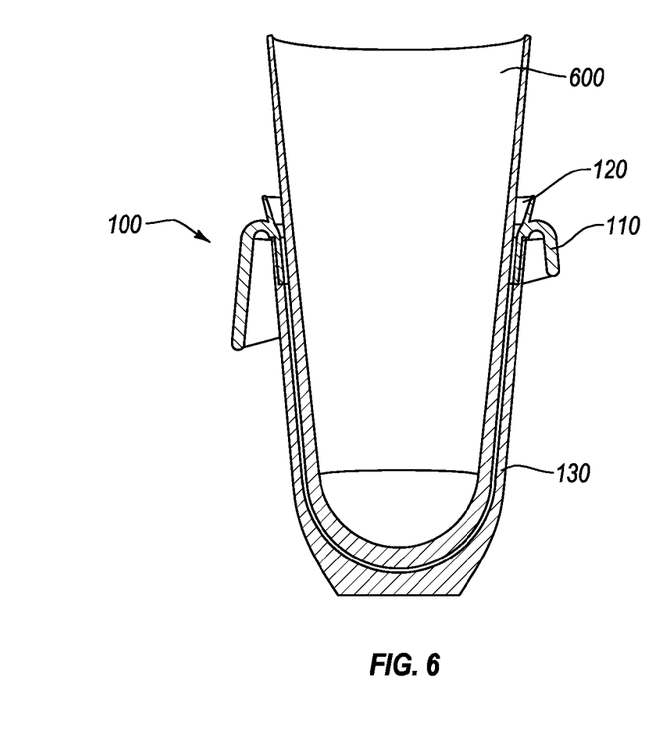
FIG. 6 shows a cross sectional view of an embodiment of the socket and attached brim attachment receiving a liner, with the brim attachment in a tensioned position.
Figure 7:
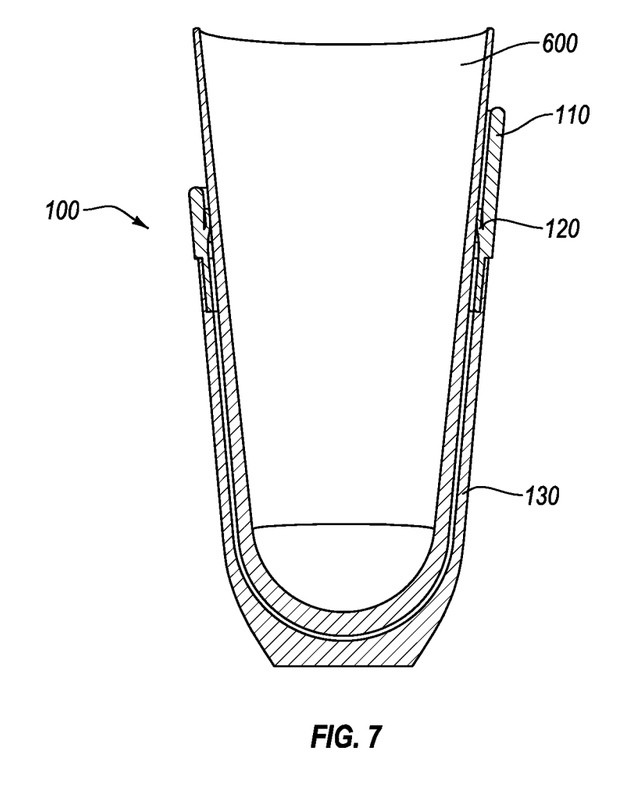
FIG. 7 shows a cross sectional view of the socket and attached brim attachment receiving a liner, with the brim attachment in a relaxed position.

FIGS. 5-7 show various stages of a brim attachment 100 being used to secure a liner and residual limb within a socket 130. FIG. 5 depicts a cross sectional view of the socket 130 and attached brim attachment 100, with the brim attachment 100 in a relaxed position. The cuff 110 is extending substantially parallel to a longitudinal axis of the socket 130 and is not being reflected about the proximal opening of the socket 130. The seal element 120 is extending inwardly towards the middle of the opening of the socket 130 positioning the seal element 120 into a sealing configuration.

FIG. 6 depicts a liner 600 inserted into the socket with the brim attachment 100 being positioned in a tensioned position. One will understand that often a liner 600 would not demonstrate the shape depicted in FIG. 6 unless a residual limb had been inserted into the liner 600. In this illustration, however, the liner 600 is shown without a residual limb for simplicity and clarity.

In FIG. 6, the cuff section 110 has been reflected about a portion of the outer surface of the socket 130. In at least one embodiment, once reflected, as depicted in FIG. 6, the cuff section 110 will remain in the illustrated position (i.e., tensioned position) until it is pushed and/or pulled upward at which time it will elastically return to a relaxed position. In at least one embodiment the cuff section 110 will not remain in any position other than a relaxed position unless force applies to the cuff section 110.

As depicted in FIG. 6, and described above, when the cuff section 110 is in the tensioned position, the seal element 120 extends outward and upward from the opening of the socket 130. In this configuration, the seal element 120 no longer functions as a sealing interface between the brim attachment 100 and the liner 600. Instead, the seal element 120 presents an expanded entry (regarding the relaxed position) into the socket 130. With the seal element 120 and cuff section 110 out of the way, a wearer of a prosthetic limb can easily insert a liner and residual limb (not shown) into the socket 130.

Once a liner 600 and residual limb (not shown) have been inserted into the socket 130, the flexible brim 110 can be returned to a relaxed position (non-reflected position). In this position, the flexible brim 110 is substantially parallel to both the socket 130 and a residual limb inserted into the socket 130. The seal element 120 is positioned in a sealing configuration such that the seal element 120 functions as a seal between the cuff section 110 and a liner 600.

Once a seal has been established a vacuum can be created between the inner walls of the socket 130 and the liner 600. One will understand that creating a vacuum within the socket 130 can provide a wearer of the prosthetic limb with improved proprioception and volume control. In view of the above disclosure, one will understand that the brim attachment can also easily release a vacuum created by the seal element 120. As depicted in FIG. 6, a vacuum can be released by pulling the cuff section 110 outward or otherwise reflecting the cuff section 110. Once the cuff section 110 is reflected, the vacuum can be released and a liner 600 and residual limb can easily be removed from the socket 130.

FIGS. 1-7 provide several components, schematics, and mechanisms for using a brim attachment 100 on a socket 130 to aid in easy donning and doffing of a prosthetic limb. Embodiments of the disclosure provide various methods of using a brim attachment 100 to increase proprioception. Embodiments of the disclosure allow a user to easily create a seal between a liner 600 and the brim attachment 100 using a seal element 120 to create a vacuum or using a uni-directional material 300 to resist the removal of a liner 600 from a socket 130. Various embodiments of the disclosure provide for easy donning or doffing of a socket 130. A wearer can pull outward or reflect the cuff section 110 such that the socket can be readily donned or doffed.

While the foregoing embodiments have been described and shown, alternatives and modifications of these embodiments, such as those suggested by others, may be made to fall within the scope of the invention. The principles described may be extended to other types of prosthetic or orthopedic devices.

The invention claimed is:

1. A brim attachment for a prosthetic socket, the socket defining an opening and inner and outer surfaces, the brim attachment having tensioned and relaxed positions, the brim attachment comprising:
   a cuff section defining an upper portion of the brim attachment and arranged to extend about and upwardly from the socket opening, the cuff section configured to move between tensioned and relaxed positions, wherein the tensioned position the cuff section is arranged to fold downwardly away from the socket opening and generally over the outer surface of the socket, wherein the relaxed position the cuff section is arranged to extend above the socket opening and generally concentric with the outer surface of the socket;
   an interface section defining a lower portion of the brim attachment and arranged to extend along a surface of the socket in both the tensioned and relaxed positions;
   a seal element protruding from an inner surface of the brim attachment and located generally at a junction of the cuff and interface sections, the seal element having a tapered thickness with a peak at an outermost portion of the seal element, the peak of the seal element arranged to extend obliquely toward a central axis of the socket and upwardly from the socket opening in the relaxed position, the peak of the seal element extends upwardly from and concentrically to the upper perimeter of the socket in the tensioned position, the seal element moves into the relaxed and tensioned positions as a result of moving the cuff section between the relaxed and tensioned positions.

2. The brim attachment of claim 1, wherein the cuff and the interface sections are formed integrally with one another from the same material.

3. The brim attachment of claim 1, wherein the cuff section defines an asymmetrical upper edge having a maximum height extending a greater distance from the socket opening than a minimum height of the upper edge.

4. The brim attachment of claim 3, wherein the maximum height is located at a first side of the socket and the minimum height is located at a side opposite the maximum height, the upper edge tapering in height from the maximum height to the minimum height.

5. The brim attachment of claim 1, wherein the interface section has a smaller thickness than a thickness of the cuff section.

6. The brim attachment of claim 1, wherein the peak forms a thinnest portion of the seal element.

7. The brim attachment of claim 1, wherein the seal element defines a base portion formed integrally with the cuff and interface sections, the base portion forming the thickest portion of the seal element.

8. The brim attachment of claim 1, wherein the cuff section is arranged to extend circumferentially about and upwardly away from an upper perimeter of the socket opening in the relaxed configuration, the interface section extending downwardly from the cuff section.

9. A brim attachment for a prosthetic socket, the socket defining an opening and inner and outer surfaces, the brim attachment having tensioned and relaxed positions, the brim attachment comprising:
   a cuff section defining an upper portion of the brim attachment and arranged to extend about and upwardly from the socket opening, the cuff section configured to move between the tensioned and relaxed positions, wherein the tensioned position the cuff section is arranged to fold downwardly away from the socket opening, wherein the relaxed position the cuff section is arranged to extend above the socket opening, the cuff section defining an asymmetrical upper edge having a maximum height extending a greater distance from the socket opening than a minimum height of the upper edge;
   an interface section defining a lower portion of the brim attachment and arranged to extend along a surface of the socket downwardly proximate the socket opening from the cuff section;
   a seal element protruding from an inner surface of the brim attachment and located generally at a junction of the cuff and interface sections, the seal element having a tapered thickness with a peak at an outermost portion of the seal element, the peak of the seal element arranged to extend obliquely toward a central axis of the socket and upwardly from the socket opening in the relaxed position, the peak of the seal element extends upwardly from and concentrically to the upper perimeter of the socket in the tensioned position.

10. A socket system including a prosthetic socket and a brim attachment secured to the socket, the socket defining an opening and inner and outer surfaces along a socket wall, the socket having a recess formed proximate the opening along the inner surface at which the brim attachment secures, the brim attachment having tensioned and relaxed positions, the brim attachment comprising:
    a cuff section defining an upper portion of the brim attachment and arranged to extend about and upwardly from the socket opening in the relaxed configuration, the cuff section configured to move between the tensioned and relaxed positions, wherein the tensioned position the cuff section is arranged to fold downwardly away from the socket opening;
    an interface section defining a lower portion of the brim attachment and arranged to extend along a surface of the socket, the interface defining a lip insertable into the recess of the socket;
    a seal element protruding from an inner surface of the brim attachment and located generally at a junction of the cuff and interface sections, the seal element having a tapered thickness with a peak at an outermost portion of the seal element, the peak of the seal element arranged to extend obliquely toward a central axis of the socket and upwardly from the socket opening in the relaxed position, the peak of the seal element extends upwardly from and concentrically to the upper perimeter of the socket in the tensioned position.

11. The socket system of claim 10, wherein the interface section has a smaller thickness than a thickness of the cuff section.

12. The socket system of claim 10, wherein the lip of the interface section is adhered along the inner surface of the socket and is flush with the inner surface of the socket in areas outside the recess such that socket defines a continuous inner surface with the interface section.

13. The socket system of claim 12, wherein a thickness of the socket outside the recess is the same as a combined thickness of the socket wall at the recess and the lip.

* * * * *